(12) United States Patent
Smith

(10) Patent No.: US 6,498,854 B1
(45) Date of Patent: Dec. 24, 2002

(54) TRANSDUCER FOR SENSING BODY SOUNDS

(76) Inventor: Clive Smith, 6571 S. Pontiac Ct., Englewood, CO (US) 80111

( * ) Notice: Subject to any disclaimer, the term of this patent is extended or adjusted under 35 U.S.C. 154(b) by 0 days.

(21) Appl. No.: 09/431,717

(22) Filed: Oct. 28, 1999

(51) Int. Cl.[7] ................................................ A61B 7/04
(52) U.S. Cl. ...................................................... 381/67
(58) Field of Search .................................. 381/67, 174

(56) References Cited

U.S. PATENT DOCUMENTS

| | | | | |
|---|---|---|---|---|
| 4,582,961 A | * | 4/1986 | Frederiksen | 179/111 |
| 4,784,154 A | * | 11/1988 | Shirley et al. | 381/67 |
| 4,986,276 A | * | 1/1991 | Wright | 128/662.4 |
| 5,006,952 A | * | 4/1991 | Thomas | 361/283 |
| 5,022,405 A | * | 6/1991 | Hok et al. | 381/67 |
| 5,932,849 A | * | 8/1999 | Dieken | 381/67 |
| 6,002,777 A | * | 12/1999 | Grasfield et al. | 381/67 |

FOREIGN PATENT DOCUMENTS

JP          10-258053 A1     9/1998

* cited by examiner

*Primary Examiner*—Forester W. Isen
*Assistant Examiner*—Laura A. Grier
(74) *Attorney, Agent, or Firm*—Colin P. Abrahams

(57) ABSTRACT

An acoustic-to-electrical transducer for sensing body sounds is disclosed. The transducer comprises a capacitive sensor, whereby a stethoscope diaphragm forms one plate of a capacitor, with the second plate of the capacitor being co-planar to the diaphragm. The capacitance of the two plates varies with the distance between them, said distance being modified by motion of the diaphragm in response to sound pressure. The sensor, circuitry, manufacturing methods and improvements are disclosed.

13 Claims, 8 Drawing Sheets

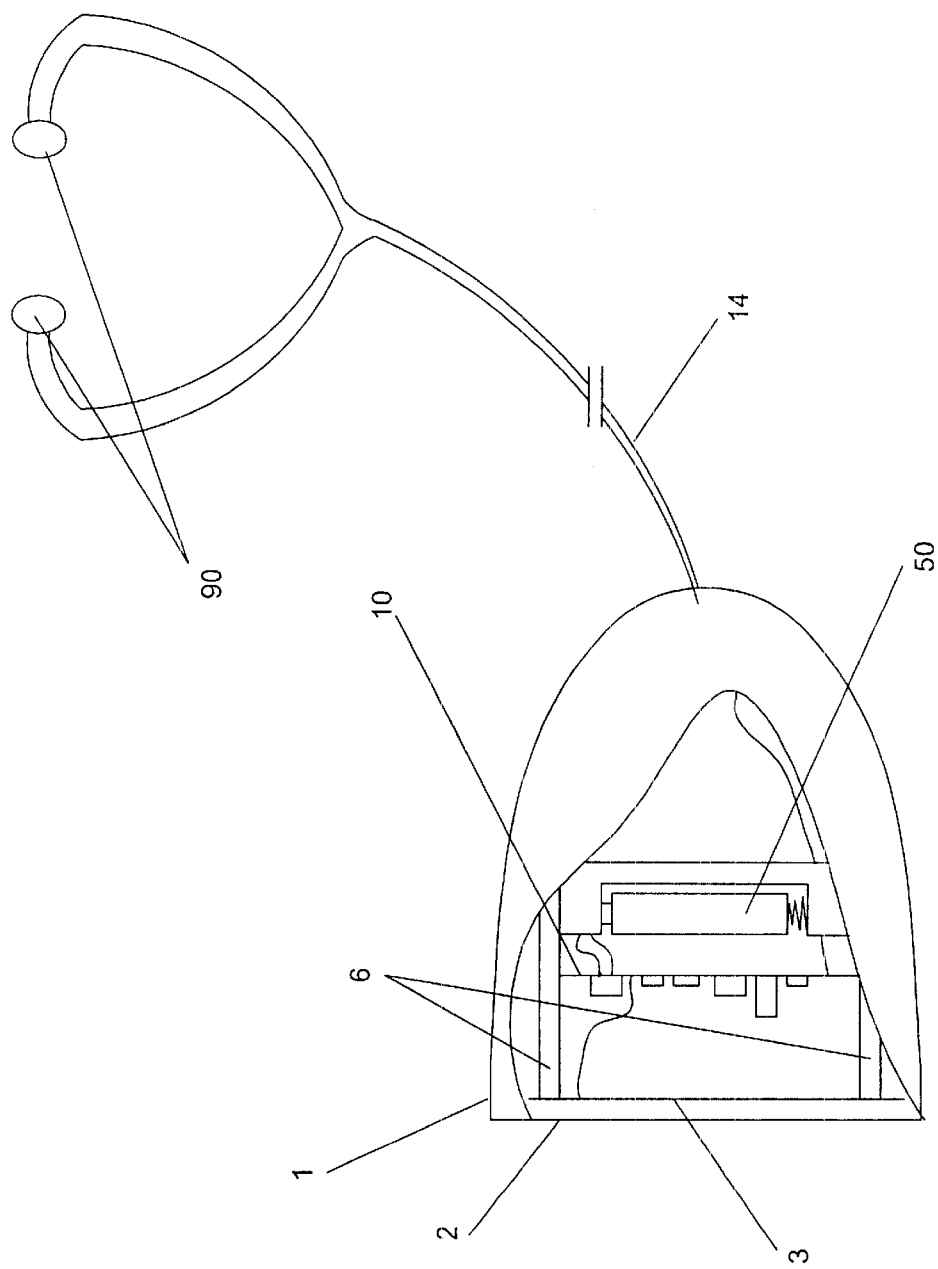

TRANSDUCER FOR SENSING BODY SOUNDS

FIELD OF THE INVENTION

The present invention relates to sensing body sounds, and more specifically, to acoustic-to-electrical transducers used for sensing body sounds, especially in stethoscopes.

BACKGROUND OF THE INVENTION

Stethoscopes are widely used by health professionals to aid in the detection of body sounds. The procedures for listening to and analyzing body sounds, called auscultation, is often difficult to learn due to the typically low sound volume produced by an acoustic stethoscope. Electronic stethoscopes have been developed which amplify the faint sounds from the body. However, such devices suffer from distortion and ambient noise pickup. The distortion and noise are largely due to the performance of the acoustic-to-electrical transducers, which differ in operation from the mechanical diaphragms used in acoustic stethoscopes.

Acoustic stethoscopes have been the reference by which stethoscope sound quality has been measured. Acoustic stethoscopes convert the movement of the stethoscope diaphragm into air pressure, which is directly transferred via tubing to the listener's ears. The listener therefore hears the direct vibration of the diaphragm via air tubes.

Existing electrical stethoscope transducers are typically one of two types: (1) microphones mounted behind the stethoscope diaphragm, or (2) piezo-electric sensors mounted on, or physically connected to, the diaphragm.

Microphones mounted behind the stethoscope diaphragm pick up the sound pressure created by the stethoscope diaphragm, and convert it to electrical signals. The microphone itself has a diaphragm, and thus the acoustic transmission path comprises stethoscope diaphragm, air inside the stethoscope housing, and finally microphone diaphragm. The existence of two diaphragms, and the intervening air path, result in excess ambient noise pickup by the microphone, as well as inefficient acoustic energy transfer. Various inventions have been disclosed to counteract this fundamentally inferior sensing technique, such as adaptive noise canceling, and various mechanical isolation mountings for the microphone. However, these methods are often just compensations for the fundamental inadequacies of the acoustic-to-electrical transducers.

The piezo-electric sensors operate on a somewhat different principle than merely sensing diaphragm sound pressure. Piezo-electric sensors produce electrical energy by deformation of a crystal substance. In one case, the diaphragm motion deforms a piezoelectric sensor crystal which is mechanically coupled to the stethoscope diaphragm, and an electrical signal results. The problem with this sensor is that the conversion mechanism produces signal distortion compared with sensing the pure motion of the diaphragm. The resulting sound is thus somewhat different in tone, and distorted compared with an acoustic stethoscope.

Capacitive acoustic sensors have been disclosed and are in common use in high performance microphones and hydrophones. A capacitive microphone utilizes the variable capacitance produced by a vibrating capacitive plate to perform acoustic-to-electrical conversion. A capacitive microphone placed behind a stethoscope diaphragm would suffer from the same ambient noise and energy transfer problems that occur with any other microphone mounted behind a stethoscope diaphragm. The present invention, however, exploits the basic principle of a capacitive transducer in a form customized for body sound sensing, in a unique manner.

SUMMARY OF THE INVENTION

According to one aspect of the invention, there is provided a acoustic-to-electrical transducer for detecting body sounds, the transducer comprising: a diaphragm having an electrically conductive surface, the diaphragm being mounted in a housing such that the diaphragm can contact a body for body sound detection; a conductive plate substantially parallel to the diaphragm, mounted within the housing, the conductive plate being positioned behind and spaced from the diaphragm to allow diaphragm motion, the diaphragm and conductive plate being connected in the of form an electrical capacitance to electrical circuitry; and a capacitance-to-electrical signal conversion means to convert capacitance changes to electrical signals.

The present invention provides an acoustic-to-electrical transducer means for the detection of body sounds, such as for use in a stethoscope. The term "body" in this specification may include living or inanimate bodies. Living bodies may include humans and animals, while inanimate bodies may include, by example only, buildings, machinery, containers, conduits and the like. The sensor operates on a capacitance-to-electrical conversion principle., The sensor detects stethoscope diaphragm movement directly, converting the diaphragm movement to an electrical signal which is a measure of the diaphragm motion. Further amplification or processing of the electrical signal facilitates the production of an amplified sound with characteristics closely resembling the acoustic stethoscope sound, but with increased amplification, while maintaining low distortion. This is a significant improvement over the more indirect diaphragm sound sensing produced by the microphonic or piezoelectric methods described above. Since the diaphragm motion, is sensed directly, the sensor is less sensitive to outside noise than the other methods described, and the signal is a more accurate measure of the diaphragm movement. In the case of the acoustic stethoscope, diaphragm movement produces the acoustic pressure waves sensed by the listener's ears, and in the case of the present invention, that same diaphragm movement produces the electrical signal in a direct manner, the signal eventually being used to drive an acoustic output transducer such as headphones, to set up the same acoustic pressure waves impinging on the listener's ears.

The present invention utilizes a capacitive sensing method. Capacitive acoustic sensors have been disclosed and are in common use in high performance microphones and hydrophones. However, the present invention uses the stethoscope diaphragm itself as one plate of the capacitive sensor which touches the body surface directly. This method of direct contact capacitive sensing of body sounds as described, is unique.

The sensor comprises a movable diaphragm with a conductive surface, and a co-planar conductive surface (electrode or plate) placed behind the diaphragm, with a space or electrolyte between the two elements. The diaphragm's conductive surface, in conjunction with the second conductive plate, form a capacitor. Movement of the diaphragm due to motion or sound pressure modulates the distance between the diaphragm and plate, producing a change in capacitance. One unique aspect of the invention lies in the fact that the stethoscope diaphragm forms one plate of the capacitor.

A feature of the invention is that the diaphragm, being the same element that makes contact with the body, is primarily sensitive to sounds emanating from the body, rather than sound transmitted through the air from ambient noise. By making contact with the body, the acoustic impedance of the sensor becomes matched to that of the body, rather than the surrounding air. Therefore, the capacitance change due to diaphragm motion is primarily due to body sounds, rather than overall ambient noise.

While a number of means are available for converting the capacitance variation to an electrical signal, the preferred embodiment performs this conversion by charging the capacitance formed by the diaphragm-plate combination to a high DC voltage, via a high resistance. This produces a somewhat constant charge on the capacitor. Movement of the diaphragm then produces a variation in the capacitance. If the capacitor charge is fixed, and the capacitance varies with time, a small AC variation in capacitance voltage is produced. This is sensed by a high-impedance amplifier, which is designed to detect the AC changes in capacitance voltage while avoiding rapid discharge of the capacitor.

A second method for detecting capacitance change is to employ the same diaphragm-plate capacitance in a high-frequency resonant or oscillation circuit, and detect changes in oscillation frequency produced by changes in the time constant of the capacitive circuit.

A third method of constructing a capacitive sensor, and sensing capacitance variation is via the use of an electret technique. This method requires that one or both of the plates of the capacitor formed by the diaphragm-plate be coated with a permanently charged material, such as an electret, material, to create a permanent electric field between the plates. Since the plate, or plates, have a permanent electric field between them, the production of a high DC charge voltage is obviated, and voltage changes can be produced due to movement without the need for a DC charge voltage produced via a circuit.

Any method of detecting capacitance change and converting such change to an electrical signal is encompassed by this invention. This invention therefore covers all such methods for detecting capacitance changes due to diaphragm motion.

It should be noted that while the preferred embodiment comprises a fixed plate behind the diaphragm, the invention includes methods whereby both plates are flexible and form a capacitance. In such a case, the basic principle applies whereby the capacitance varies due to sound pressure from the body, but the second plate is not necessarily rigid.

In the preferred embodiment, the fixed plate is mounted behind the diaphragm. In order to ensure acoustic isolation from external sounds, the fixed plate should preferably be mounted through a means which acoustically isolates it from the housing, or uses a means intended to prevent the fixed plate from vibrating. This is an important improvement which enhances noise isolation.

A variation of the basic principle of operation is to create two capacitors, by having the conductive diaphragm as described, with a conductive plate behind the diaphragm forming one capacitor, and a third plate behind the second, forming a second capacitor. The diaphragm and third plates are charged, while the second, middle plate is connected to an amplifier circuit. This two-capacitor method operates on essentially the same principle, whereby voltage across a charged capacitor varies in response to distance between plates, one plate being formed by the diaphragm.

A further feature of the invention, is the method for constructing and producing the diaphragm. The diaphragm material must be flexible, and conduct electricity, in order to perform as a variable capacitor plate sensitive to sound pressure. This electrically conductive surface is preferably, but not necessarily, electrically insulated from the surface of the diaphragm that touches the body, for both safety and interference-prevention purposes.

A further feature of the preferred embodiment is the capacitive sensing circuitry connected to the diaphragm-plate capacitor. In the preferred embodiment, the circuit comprises two critical elements: (1) a high voltage DC bias generator with very high impedance, and (2) an AC amplifier with very high impedance to sense AC voltage changes without discharging the capacitor.

The invention also includes methods for signal amplitude control, DC charge voltage control to preserve battery power, and construction and manufacture of the capacitive sensor.

BRIEF DESCRIPTION OF THE DRAWINGS

FIG. 9 shows in schematic form and not to scale a stethoscope including the sensor of the invention.

DETAILED DESCRIPTION OF THE PREFERRED EMBODIMENTS

Figure 1:
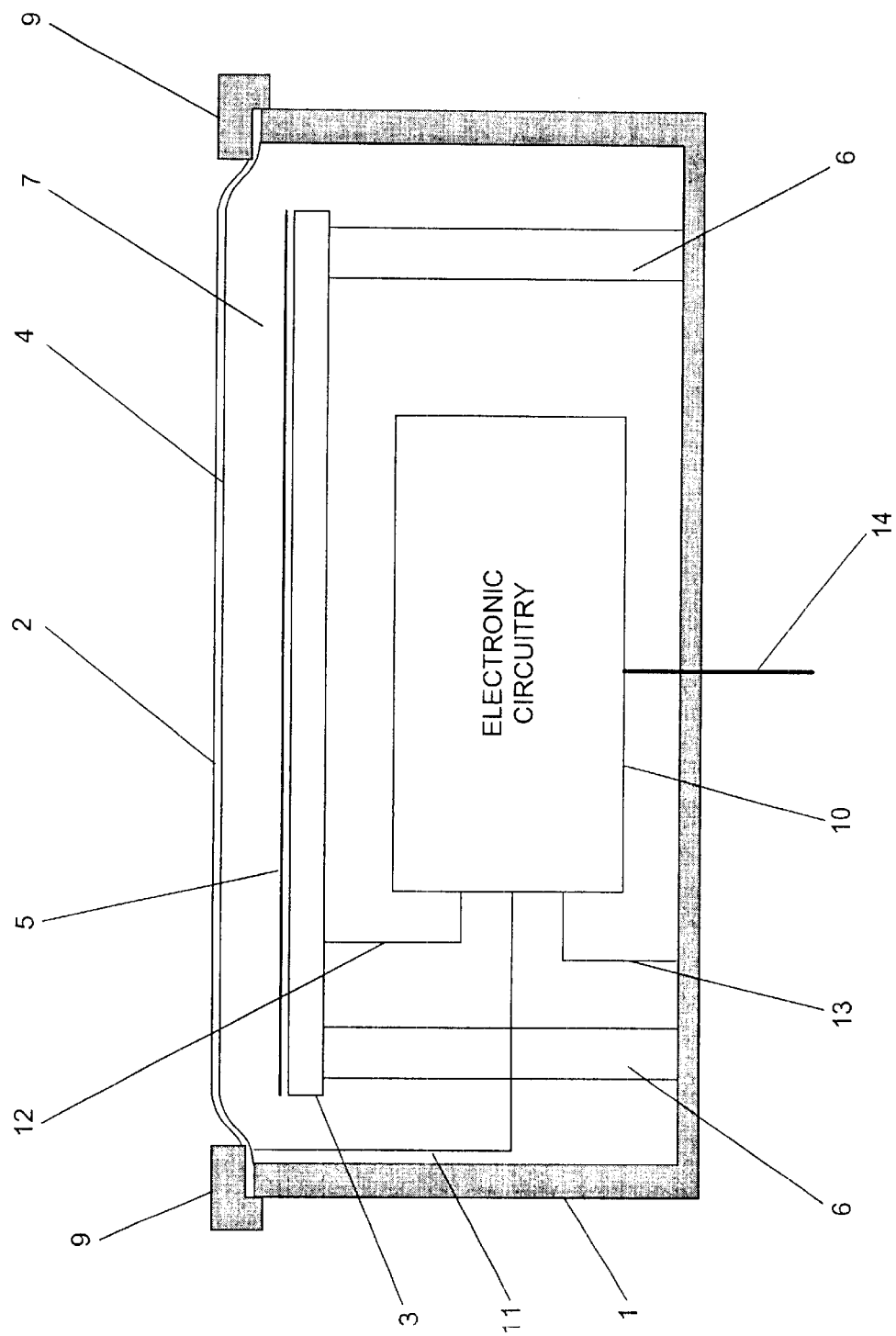
FIG. 1 shows the basic mechanical structure of the invention in one preferred embodiment.

With reference to the drawings, FIG. 1 shows the basic mechanical structure of the invention in its preferred embodiment. A housing 1 contains a capacitive sensing mechanism comprising a movable flexible diaphragm 2, with electrically conductive surface 4, such surface preferable being on the inner surface, placed co-planar to an electrically conductive plate 3, with some intervening space 7 filled with air or an electrically nonconductive fluid or gaseous substance. The diaphragm 2 and plate 3 form a capacitor. Motion of the diaphragm 2 due to sound pressure varies the distance between diaphragm 2 and plate 3, thereby varying the capacitance of the diaphragm-plate capacitance, since the capacitance is inversely proportional to the distance between the diaphragm 2 and the plate 3. A unique aspect of the invention is that the stethoscope diaphragm 2 forms one plate of a capacitive sensor, whereby the motion of the diaphragm 2 varies capacitance, which then varies other circuit parameters in an electronic circuit, to generate a time-varying electrical signal measuring diaphragm motion. The diaphragm motion is then a measure of the sound being detected, and hence the invention forms an effective body sound sensor.

In a preferred embodiment, the diaphragm 2 is mounted to the housing 1 via an attachment means 9 which provides acoustic isolation or significant acoustic wave attenuation from the housing 1. This can be achieved by selection of a sound absorbing material for the attachment 9, and/or by shaping the diaphragm 2 such that vibration from the outside circumference of the diaphragm 2 is not coupled to the major surface area thereof. The plate 3 is mounted behind the diaphragm via mounting brackets 6, which provides acoustic isolation or attenuation from the housing in order to reduce ambient noise pickup by preventing the plate 3 from vibrating.

The diaphragm 2 is mechanically housed such that it can be placed in physical contact with a body to sense sound from the body by direct physical contact, rather than via a fluid or air medium as is typical of microphones and hydrophones. This imposes on the diaphragm 2 a preferred property that it be capable of a displacement significantly larger than that typically required for a microphone or hydrophone diaphragm, making space 7 larger than that typical of air microphones or hydrophones. In a preferred embodiment, the distance between diaphragm 2 and plate 3 typically exceeds 0.5 mm, although smaller distances may be possible. This is a somewhat unique characteristic of this sensing application, resulting in a very low diaphragm-plate capacitance.

In a preferred embodiment of the invention, a high voltage potential is generated between the diaphragm 2 and plate 3. Using such a method, electrical insulation is required of a number of elements in the invention. A high-dielectric insulator 5, made from substances such as Mylar® film produced by E.I. Du Pont, or Ultem® film manufactured by General Electric, is optionally placed between the diaphragm 2 and plate 3. This reduces electronic noise caused by discharge of the capacitance across the space 7 between the diaphragm 2 and plate 3. While the insulator 5 is not essential to sensor operation, it enhances sound quality. The plate 3 is mounted via a mounting bracket 6 to the housing 1, such mounting bracket being made of a material which provides high electrical isolation, such as nylon or Teflon®. This prevents trickle discharge of the plate 3. The preferred electrical insulation requirements stated above are relevant to the embodiment of the invention that requires a high voltage potential between the plate 3 and diaphragm 2. Other embodiments do not necessarily require such high quality electrical insulation, since they might rely on methods of capacitance measurement which does not require a significant DC voltage on the capacitance.

The electrical connections are shown in FIG. 1, for one embodiment of the invention. An electronic circuit 10 is preferably mounted within housing 1, with connection 13 to the housing 1, connection 11 to the diaphragm conductive surface 4, and connection 12 to, the plate 3. External power and signal connections are provided via connection means 14. The principle of operation of the sensor does not require that the associated circuitry be placed within housing 1. However, best performance is obtained by placing amplifier circuitry close to the sensing capacitance.

Figure 2:
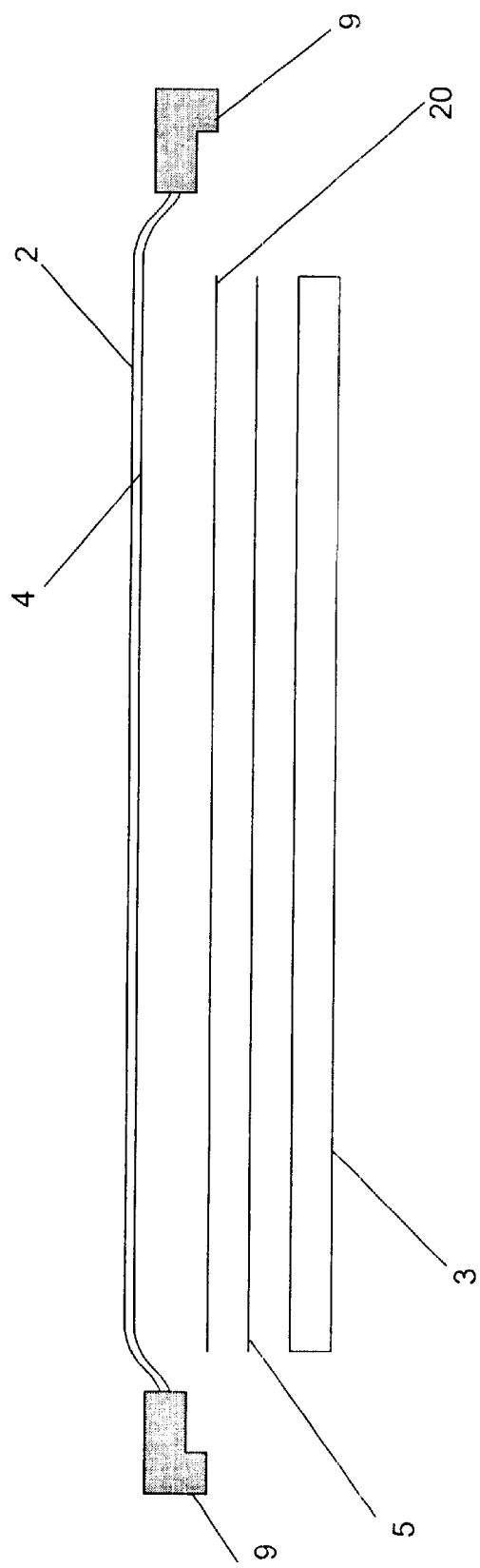
FIG. 2 shows an second embodiment of the sensor capacitive elements of the invention, whereby a double-capacitance is formed.

FIG. 2 shows an alternative embodiment of the sensor capacitive elements of the invention, whereby a double-capacitance is formed. Diaphragm 2 has a conductive surface 4, which forms a capacitance with plate 20, which is comprised of a conductive material. The plate 20 then forms a second capacitance with plate 3, while optional insulation 5 is placed between plate 20 and plate 5. The diaphragm 2 is once again mounted to the housing by a mounting clamp 9. The double capacitance method operates on a similar principle of operation to the embodiment of FIG. 1. However, the circuit connections are somewhat different, as described in further detail below.

Figure 3:
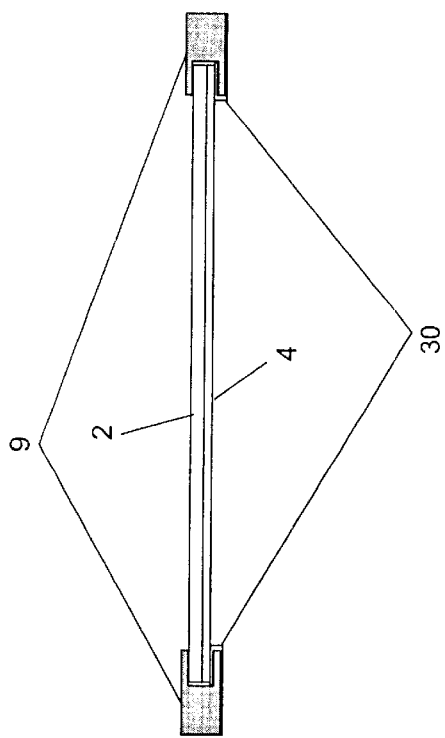
FIG. 3 shows another embodiment of a mounting means for the diaphragm.

FIG. 3 shows an alternative mounting clamp 9 for the diaphragm 2. the mounting clamp 9 is a circular ring shown in cross section. The material from which mounting clamp 9 is made is a sound absorbing substance such as rubber, which prevents vibration from the housing 1 in. FIG. 1 from reaching the diaphragm 2 surface. However, the diaphragm has an electrically conductive surface 4 which must be connected to electronic circuitry as indicated in FIG. 1 by connection 11. This connection 11 is achieved, as shown in FIG. 3, by providing a conductive path 30 on the mounting clamp 9. FIG. 3 shows one configuration for achieving acoustic isolation and electrical connection to the conductive surface 4 of the diaphragm 2. If the mounting clamp 9 has a different cross section, or is manufactured from a conductive rubber, the goals of acoustic isolation and electrical connection may still be met.

Figure 4:
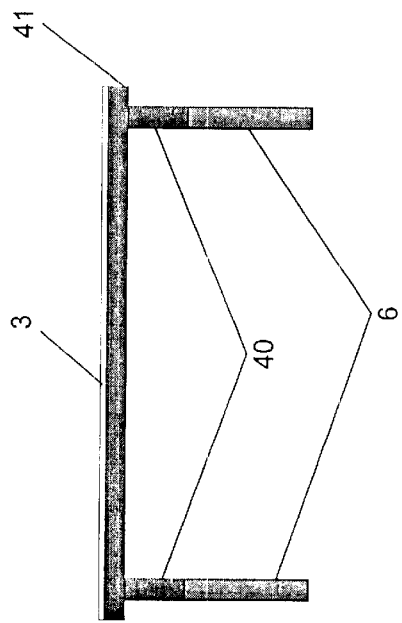
FIG. 4 shows means of ambient sound isolation for the capacitive plate in further detail.

FIG. 4 shows an important aspect of ambient sound isolation for the plate 3 in more detail. The plate 3 should not vibrate due to housing or external vibrations such as might be produced by ambient noise or handling-of the housing 1. The plate 3 must therefore be acoustically isolated from ambient noise sources. This may be achieved by a number of means. A mounting bracket 6 may be constructed with a section 40 which is manufactured from an acoustically absorbent material so that vibrations are attenuated by the section 40. Note that the mounting bracket 6 and the sections 40 are shown as vertical posts. Such mounting may also be achieved by surfaces molded into the housing 1 to support the plate 3, or other means of attachment of the plate 3. The invention simply requires that the plate 3 be acoustically isolated from the housing 1 for optimal performance. FIG. 4 also shows a second alternative to acoustic isolation for the plate 3. The plate 3 may be mounted on an acoustically absorbent material surface 41, such that vibration in the mounting bracket 6 is attenuated by a surface 41. A third method of acoustic isolation is to manufacture the plate 3 from a conductive foam or other electrically conductive, but acoustically absorbent material. The above three methods provide the same function—to acoustically isolate the plate 3. Other methods may be applied to achieve the same goal.

Figure 5:
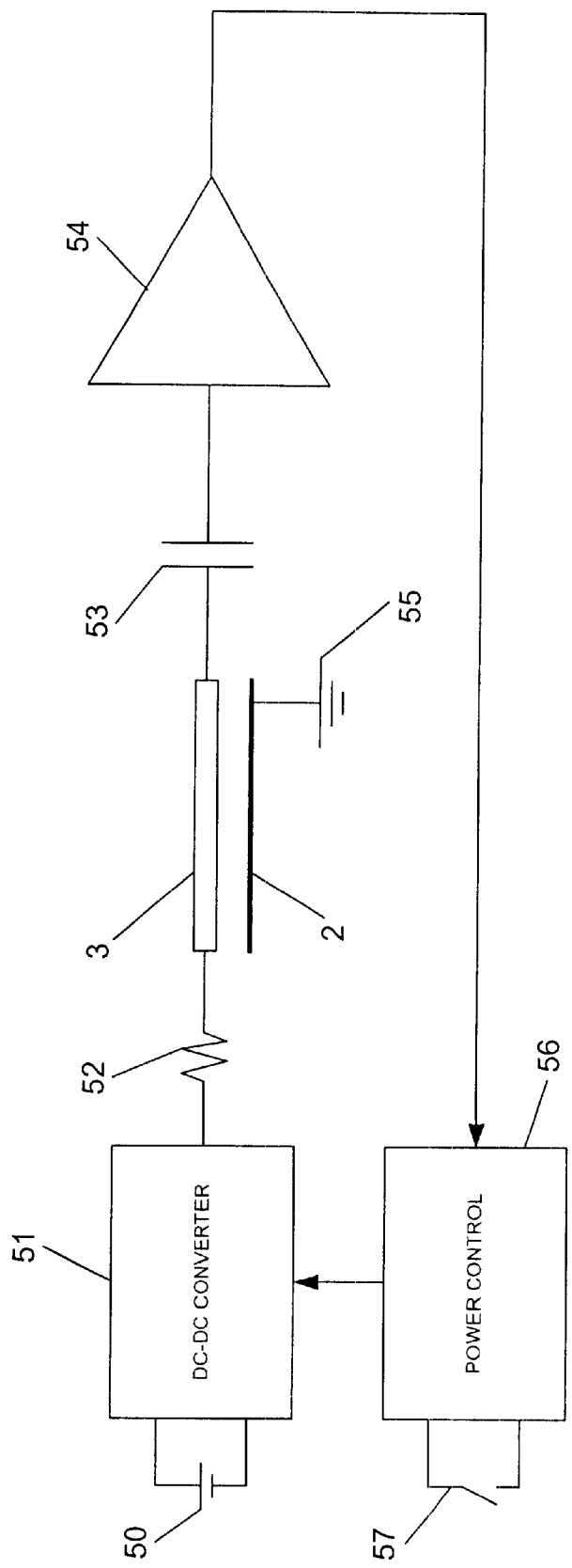
FIG. 5 shows the overall circuit topology of the sensor when used with a DC-DC charging circuit and associated function.

The method of operation of the preferred embodiment is to develop an electric field in the capacitor formed by the diaphragm 2 and the plate 3 shown in FIG. 1. There are a number of methods for creating this electric field. In a preferred embodiment, a DC source 51, which is a DC-DC boost circuit, is connected to the capacitance via a high-impedance connection 52 as shown in FIG. 5. The DC-DC converter 51 converts low voltage from battery 50 to a high voltage. A voltage of greater than 50V is desired, and significantly higher voltages, on the order of 600V–1000V, are feasible in the device. Larger voltages produce larger gain in the mechanical displacement to electrical signal transfer function. The high voltage passed via resistor 52 to the plate 3 results in the plate. 3 being at a high voltage potential relative to the diaphragm 2, which is placed at ground reference potential 55 in a preferred embodiment,, since this provides electromagnetic shielding as well as functioning as a capacitive plate. An amplifier 54 is connected to the capacitance sensor via a capacitance, 53, which isolates the high DC voltage on the plate 3 from the amplifier, while passing time-varying voltage caused by modulation of the diaphragm-plate distance. The input impedance of the amplifier 54 must be significant, in order to allow low frequencies to be passed by the capacitor 53.

Circuit functions for the high voltage implementation of the invention are shown in FIG. 5. The plate 3 is charged by the high potential voltage relative to the diaphragm 2 by DC-DC converter 51. Changes is distance between the diaphragm 2 and plate 3 produce a change in the AC, or time-varying voltage across the capacitor, with high resistance 52 and high input impedance of amplifier 54 preventing the capacitor charge from changing too rapidly. The change in the time-varying voltage across the capacitance is amplified by the amplifier 54, to produce a low-impedance time-varying signal which is a measure of capacitance change, and hence diaphragm motion.

In certain embodiments, the capacitance of the diaphragm-plate capacitor can be extremely low, on the order of 10 pico-Farads. This results in a very small time constant when the capacitance is connected to external circuitry. An important aspect of the high voltage embodiment of the sensor, is the use of very high-impedance DC charging circuitry, and signal amplification circuitry. In a preferred embodiment, this impedance is preferably above 400 Meg Ohms in both the case of the DC charger and the signal amplifier input, although lower impedances are possible. Thus, in FIG. 5, resistance 52 or the source resistance of DC source 51, and the input impedance of amplifier 54, must all be high impedances.

The housing is preferable placed at ground potential, to act as a shield. Shielding requires that the housing 1 be fabricated from an electrically conductive material, or that a conductive surface by applied to the housing 1. The housing 1 and diaphragm 2 therefore form a shielded cavity for the sensor and electronics. It should be noted that either plate 3 or diaphragm 2 may be placed at a high potential, since it is the charge on the capacitance that is of importance, not the polarity. Note that ground 55 is a relative circuit ground connection, not physically connected to earth ground.

Stethoscopes are typically portable instruments, operated on battery power. A further extension of the invention is in the minimization of power consumption. The DC voltage applied across the diaphragm-plate capacitance in the preferred embodiment is generated from a low-voltage source 50 in a typical battery operated device, as shown in FIG. 5. Since the time constant of the capacitive circuit is, by necessity, sufficiently large to allow frequencies below 100 Hz to be sensed, the DC charge on the sensing capacitance remains at an elevated voltage level for some period of time. Therefore, the DC charge circuit 51 may be operated on a pulsed, or intermittent basis, or indeed shut off, once the DC charge is generated on the capacitor plates. This offers substantial power savings over operating the DC charge circuit continuously, providing the preferred embodiment with substantially longer battery life than a continuously operated DC source would provide. The power control circuit 56 is able to control the high voltage level produced by the DC-DC converter 51 for the purposes of low power operation.

Power control function 56 is operated by either a switch means 57, or automatically by sensing the amplifier 54 output signal. Switch means 57 can also take the form of a control signal from a control microprocessor. In the automatic power control mode, the power control function detects whether the diaphragm is in contact with a body by performing signal processing on the amplifier output signal. There are a number of methods for detecting diaphragm-body contact. One method is to detect a heartbeat waveform. A preferred method is to sense low frequency signal energy in the amplifier output, since this is typically absent when the diaphragm is not in contact with a body.

Since the output signal amplitude from the amplifier 54 is dependent on the DC voltage, the power control function 56 may also be employed to monitor amplifier output and act as an automatic or manual gain control for the sensor, adjusting DC voltage to control amplifier signal output amplitude. This provides the advantage of preserving battery power, as well as providing consistent signal levels. Further, while gain control may be provided at later stages of amplification, there is an advantage to adjusting front end signal level to avoid clipping and to maximize signal-to-noise ratio of the overall amplification process.

Automatic gain control is also optionally implemented in amplifier 54. This is especially important as a means of preventing excessively loud signals from being generated. Amplifier 54 thus optionally includes an automatic muting or attenuation means which is triggered by significant signal levels. These transients typically occur when the diaphragm makes or breaks contact with a body, or when the diaphragm is moved across a body.

Figure 6:
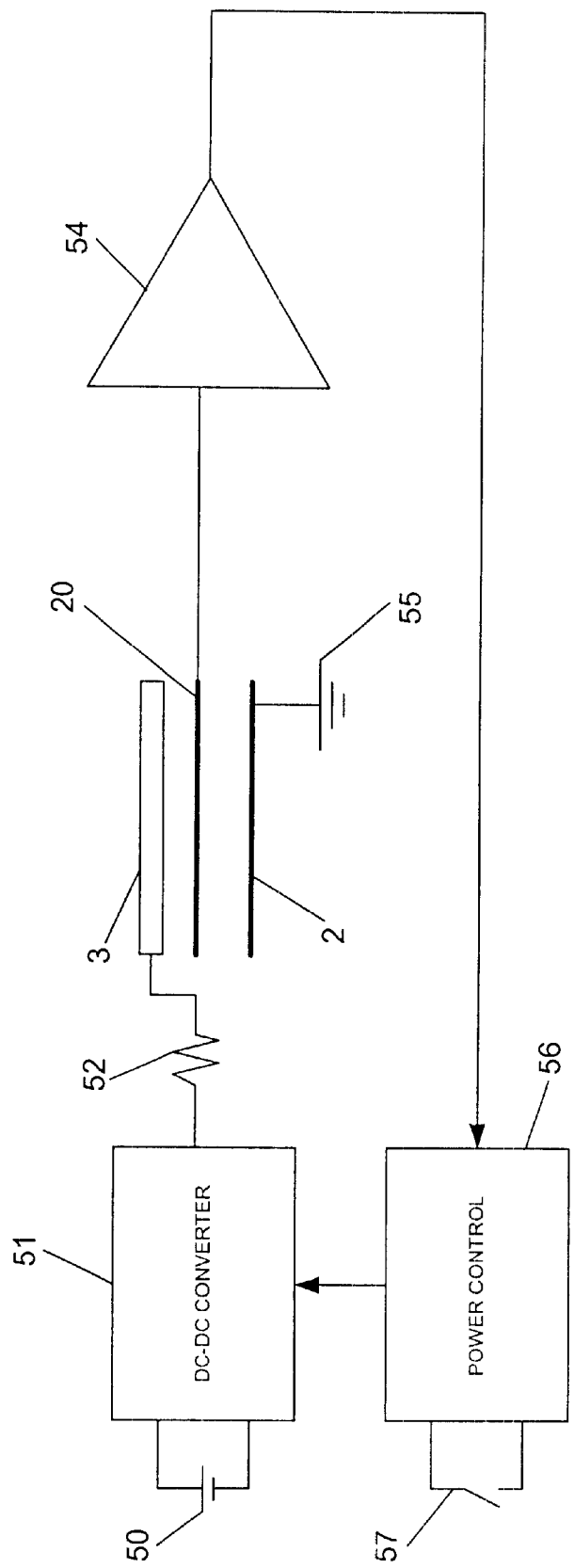
FIG. 6 shows a triple plate capacitance form of the sensor.

An alternative method of creating a capacitive sensor is shown in FIG. 2, with electrical connections shown in FIG. 6. In this implementation, sensor plate 20 is connected to the amplifier input, while plate 3 is at a high voltage as before, and diaphragm 2 is at ground reference potential 55 as before. Circuit operation is as described previously. However; the capacitance formed by plate 20 and the diaphragm serves the dual purpose of sensing and isolating the high DC voltage on plate 3 from reaching the amplifier.

Figure 8:
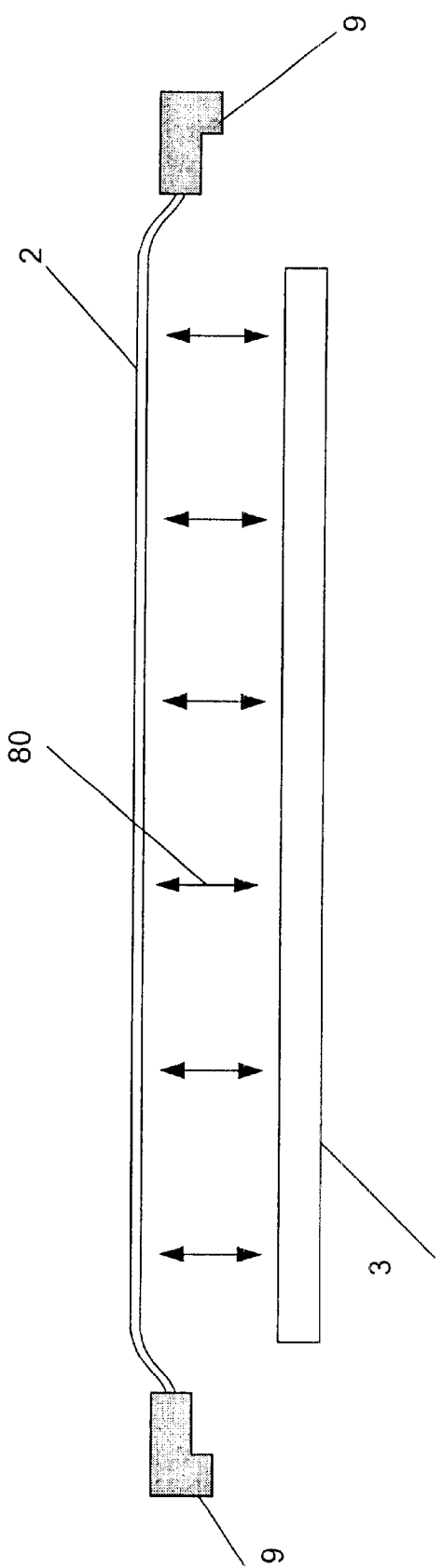
FIG. 8 shows the sensor wherein the diaphragm, plate, or both are permanently charged such that an electric field exists between the plates obviating the need for a capacitive charging circuit.

An alternative method of establishing a voltage across the diaphragm 2 and plate 3 is shown in FIG. 8 whereby diaphragm 2, plate 3 or both are fabricated with an electret or permanently charged material that maintains a permanent surface charge on one or both elements, setting up an electric field 80 with no external DC drive circuitry. This has the significant advantage that no DC-DC converter is now required, and the time-varying voltage across the diaphragm-plate capacitance may be amplified directly. This method is commonly used in small low cost electret condenser microphones. However, the present invention is unique in that one of the capacitive plates forms a stethoscope diaphragm, allowing physical contact with the body from which sound is to be detected. The manufacture of an electret implementation may be achieved by adhering an electret material to the inside of the diaphragm. Alternatively or additionally, plate 3 may be constructed with an electret surface, or an electret material may be adhered to plate 3. The salient issue is that an electric field must exist between the diaphragm 2 and plate 3, and the invention includes any means by which such a field may be created, either actively using a DC power source, or by using materials which set up a permanent electric field between diaphragm 2 and plate 3.

Figure 7:
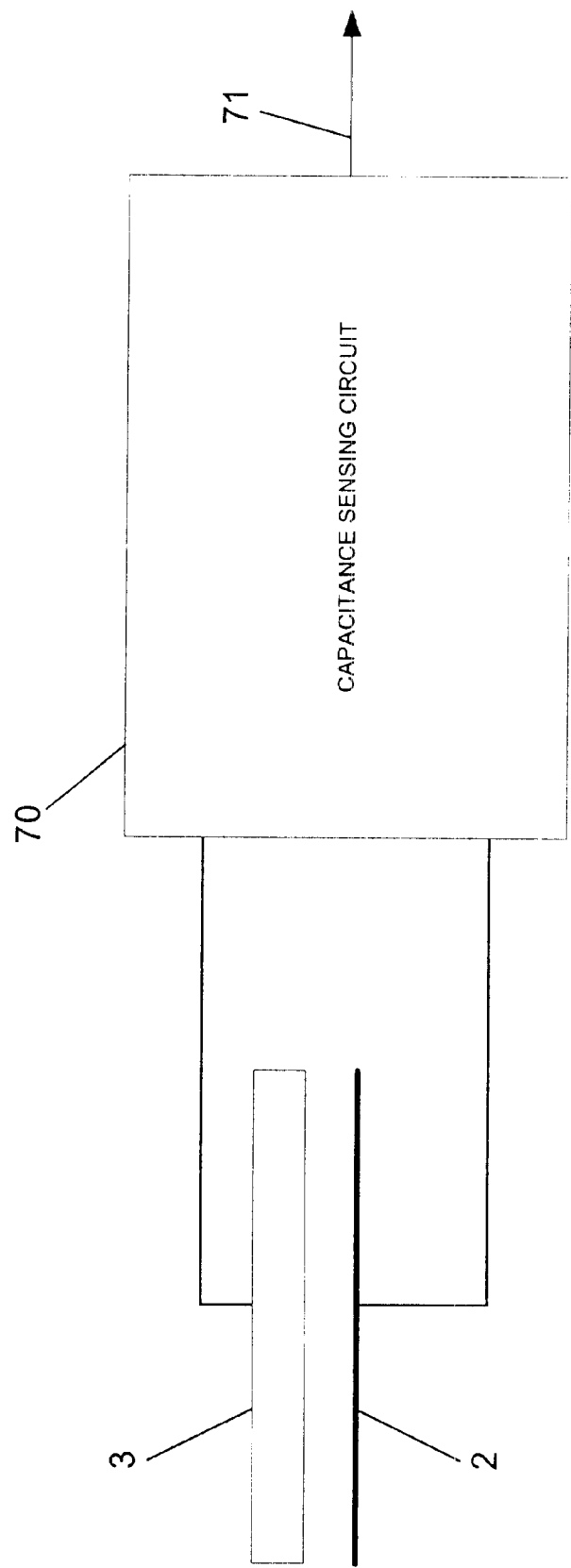
FIG. 7 shows the sensor used in a generalized capacitive sensing circuit.

An alternative method of sensing capacitive, change in the sensor is shown in FIG. 7. The plate 3 and diaphragm 2 conductive surfaces are connected to a capacitance sensing circuit 70. The output 71 is an electrical signal, or digital message which transmits the capacitance measurement as a function of time. There are a number of methods of sensing capacitance change due to diaphragm displacement. A few examples are:

a. Connecting the diaphragm-plate capacitance to an oscillator, and converting frequency variation due to capacitance change into a voltage representative of diaphragm motion.

b. Connecting the capacitance to a resonant circuit, and measuring changes in resonant characteristics with changes in capacitance.

c. Connecting the capacitance to a charging circuit, whereby the charging and/or discharging time of the circuit are converted to a voltage measurement representative of capacitance change.

d. Connecting the capacitor to a digital measurement and conversion means, whereby capacitance change results in changes in pulse width or digital values.

e. Connecting the capacitance as a timing element in an analog-to-digital converter circuit whereby digital codes are a function of the-capacitance.

All of these methods are based on the fundamental aspect of the invention whereby a capacitance is formed by the diaphragm in conjunction with another element, providing a direct transducer means from diaphragm motion to-capacitance change, to electrical measurement. In essence, the above methods use the capacitance as an element in a circuit whose time-constant affects electrical waveforms.

FIG. 9 shows in schematic form only a stethoscope with the sensor or transducer of the invention. The sensor is much the same as that illustrated in FIG. 1, with the sensor elements shown enlarged in a cutaway view. The housing 1 (shown enlarged and not to scale compared to the remainder of the stethoscope, and partially cut away) houses the elements of the sensor and associated components. The diaphragm 2 is mounted such that it can easily be placed in proximity to a body for sensing sounds. A plate 3 is mounted via a mounting bracket 6 placed behind the diaphragm 2, and parallel to it. Electronic circuit 10 is placed within the housing 1, and powered by a power source 50. An electrical connection 14 transmits audio signals to audio output transducers 90. Further details of the sensor are shown in FIG. 1 and other drawings, and may not be visible in the embodiment as illustrated in FIG. 9.

Note that FIG. 9 illustrates just one embodiment of the invention as used in a stethoscope. Various methods of housing the sensor, placing electronic circuitry within the same or different housing, partitioning electronic circuit functions within the same or different housing, and communicating the signals to the audio transducer are possible without deviating from the fundamental structures and methods disclosed herein.

Stethoscope diaphragms are subject to long term wear and breakage. In a mechanical stethoscope, replacement of the diaphragm is a simple process. In the case of a capacitive diaphragm as described in this invention, it is potentially beneficial to encapsulate the diaphragm 2 and plate 3 in FIG. 1, along with some electronic circuitry 10, in a sealed container that can be easily removed from the main body of the stethoscope. This allows the diaphragm and associated components to be replaced simply, while maintaining a sealed environment for high voltage, fluid, or other elements of the capacitive sensor which exist behind the diaphragm, and which are best kept sealed from atmospheric contaminants, or should not be touched by users. The invention thus allows for such elements of the invention to be housed in such a sealed housing, for convenient replacement or repair.

The sensor, enclosed in housing 1, can be used as a peripheral audio sensing device, which can be connected to an external audio recording, transmission or amplifying and reproduction means. Alternatively, housing 1 is physically attached to a stethoscope, and forms part of the overall stethoscope housing.

While the preferred embodiment is in the form of a capacitive sensor with a moving diaphragm and fixed plate, it is feasible to form a capacitor with both electrodes being flexible. Such a design includes a diaphragm capacitance formed by two flexible surfaces separated by a dielectric that allows modulation of the distance between the two electrodes due to motion of the two-plate diaphragm. The invention is thus intended to cover any method that comprises a diaphragm acting as part of a capacitive sensor.

What is claimed is:

1. An acoustic-to-electrical transducer for detecting body sounds, the transducer comprising:

a diaphragm having an electrically conductive surface, the diaphragm being mounted in a housing such that the diaphragm can make contact with the body and vibrate in response to body sounds;

a fixed conductive plate substantially parallel to the diaphragm, mounted within the housing, the conductive plate being positioned at a distance about or exceeding 0.5 mm from the diaphragm, the diaphragm conductive surface and fixed conductive plate forming two plates of a capacitor and connected in the form of an electrical capacitance to electrical circuitry; and a capacitance-to-electrical conversion means to convert diaphragm-plate capacitance changes due to body sound vibration to electrical signals.

2. The transducer according to claim 1, wherein the diaphragm comprises a flexible electrically-insulated substrate with electrically-conductive material deposited or adhered on an inner plane.

3. The transducer according to claim 1, wherein the capacitance is charged to a DC charge voltage by a DC to DC boost circuit, said boost circuit boosting an input DC supply voltage to a significantly higher DC charge voltage.

4. The transducer according to claim 3, wherein the DC to DC boost circuit can be operated intermittently to reduce battery power consumption.

5. The transducer according to claim 3, wherein the DC to DC boost circuit DC charge voltage magnitude is adjustable as a function of electrical signal amplitude or frequency characteristics of the output signal of the capacitance-to-electrical signal conversion means.

6. The transducer according to claim 1, wherein the diaphragm conductive surface is connected to circuit ground potential to provide electromagnetic shielding for the transducer.

7. The transducer according to claim 6, wherein a housing conductive surface is connected to circuit ground potential such that the diaphragm and housing conductive surfaces form an electromagnetically-shielded cavity for electrical circuitry housed within said cavity.

8. The transducer according to claim 1 further comprising means to create a permanent static electric field between the diaphragm and conductive plate.

9. The transducer according to claim 1, wherein the housing which includes the diaphragm and conductive plate forms a removable module which is attachable to or detachable from a stethoscope body, and includes means for mechanically and electrically coupling the module to a stethoscope body.

10. The transducer according to claim 1 wherein the mounting means for the diaphragm and fixed conductive plate include acoustic isolation means to reduce vibrations of the diaphragm or conductive plate due to ambient sound; and electrical connection means to connect diaphragm-plate capacitance to capacitance-to-electrical conversion means.

11. The transducer according to claim 1 wherein the capacitance-to-electrical conversion means includes one of the following steps for converting capacitance changes to electrical signals: (a) Varying the frequency of oscillation of an oscillator as a function of capacitance, (b) Varying the time constant of a circuit as a function of changing capacitance, (c) Generating a digital output signal which is a function of capacitance.

12. The transducer according to claim 1, wherein the space between the diaphragm conductive surface and fixed conductive plate further includes a layer of high dielectric electrical insulation material.

13. An electronic stethoscope including an acoustic-to-electrical transducer for detecting body sounds, the transducer comprising:

a stethoscope diaphragm having an electrically conductive surface, the diaphragm being mounted in a stethoscope chestpiece such that the diaphragm can contact the body for body sound detection and vibrate in response to body sounds;

a fixed conductive plate substantially parallel to the diaphragm, mounted within the chestpiece, the conductive plate being positioned at a distance about or exceeding 0.5 mm from the diaphragm, the diaphragm conductive surface and fixed conductive plate forming two plates of a capacitor and connected in the form of an electrical capacitance to electrical circuitry;

a capacitance-to-electrical signal conversion means to convert diaphragm-plate capacitance changes due to body sound vibrations to electrical signals;

the stethoscope further comprising signal amplification means and at least one electrical-to-acoustic transducer connected to signal amplification means, to reproduce body sounds as detected by said transducer.

\* \* \* \* \*